United States Patent [19]

Packard et al.

[11] Patent Number: 4,646,742

[45] Date of Patent: Mar. 3, 1987

[54] ANGIOPLASTY CATHETER ASSEMBLY

[75] Inventors: Brian M. Packard, Plymouth; David J. Parins, St. Paul; Mark A. Rydell, Long Lake, all of Minn.

[73] Assignee: Angiomedics Incorporated, Plymouth, Minn.

[21] Appl. No.: 822,385

[22] Filed: Jan. 27, 1986

[51] Int. Cl.$^4$ .............................................. A61M 29/02
[52] U.S. Cl. ................................. 128/344; 128/348.1; 604/102
[58] Field of Search ............... 122/344, 348.1; 604/96, 604/102

[56] References Cited

U.S. PATENT DOCUMENTS

| | | | |
|---|---|---|---|
| 4,004,588 | 1/1977 | Alexander | 604/96 X |
| 4,024,873 | 5/1977 | Antoshkiw et al. | 604/96 |
| 4,413,989 | 11/1983 | Schjeldahl et al. | 604/96 |
| 4,419,095 | 12/1983 | Nebergall et al. | 604/96 |
| 4,483,340 | 11/1984 | Fogarty et al. | 128/344 |
| 4,496,345 | 1/1985 | Hasson | 604/102 X |
| 4,545,390 | 10/1985 | Leary | 604/96 X |
| 4,582,181 | 4/1986 | Samson | 128/348.1 |

OTHER PUBLICATIONS

*The New England Journal of Medicine,* "Nonoperative Dilahon of Coronary-Artery Stenosis", vol. 301, No. 2, pp. 61-68 (Jul. 1979), Gruntzig, et al.

*Primary Examiner*—Albert J. Makay
*Assistant Examiner*—Steven E. Warner
*Attorney, Agent, or Firm*—Orrin M. Haugen; Thomas J. Nikolai; Frederick W. Niebuhr

[57] ABSTRACT

An angioplasty catheter having an outer tubular member and a coaxially aligned inner tubular member. The outer tube is of a first predetermined diameter over a majority of its length, but then tapers down, in a transition zone, to a second predetermined diameter less than the first and which extends to the catheter's distal tip. The inner tube has a distal end shaped to mate with the inside surface of the outer tube in the transition zone to form a seal when the inner tube is advanced in the distal direction. An expander is secured to the outer tube and inflatable by perfusing a fluid in the zone between the outer and inner tubes and through ports formed through the wall of the outer tube in the transition zone. By manipulating the proximal end of the inner tube, blood or other fluids may be perfused or exasperated and made to inflate or deflate the expander, the distal end of the inner tube acting as a valve, seating with the inner surface of the outer tube in the transition zone. The inner tube may be removed completely for maximum perfusion or for replacement with a guide wire or an optical fiber when performing laser angioplasty. The hub on the proximal end of the catheter body facilitates the manipulation of the aforementioned valve and the introduction of a perfusant along the length of the catheter body.

9 Claims, 4 Drawing Figures

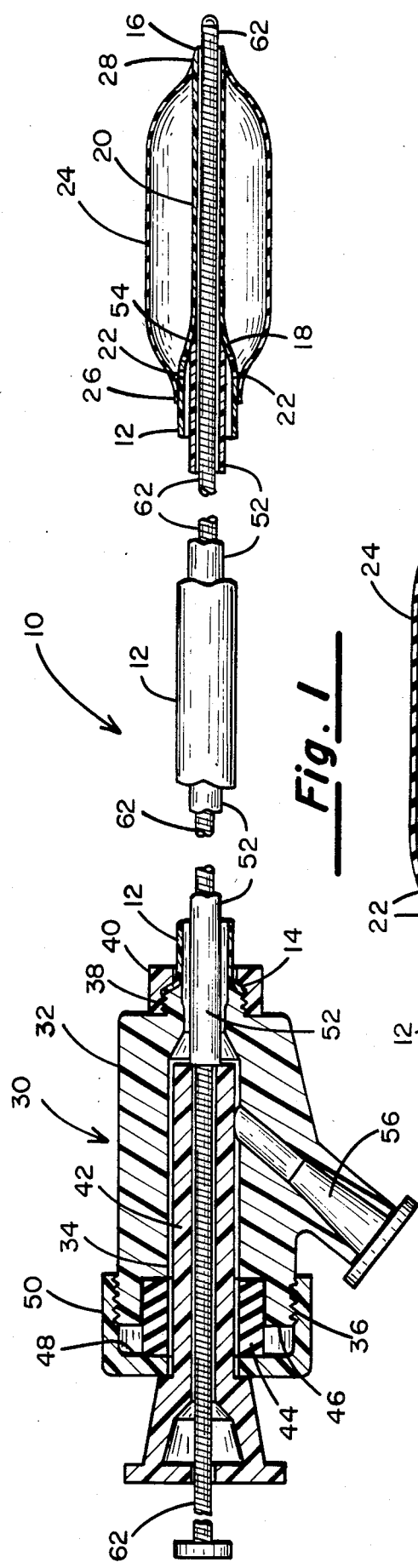
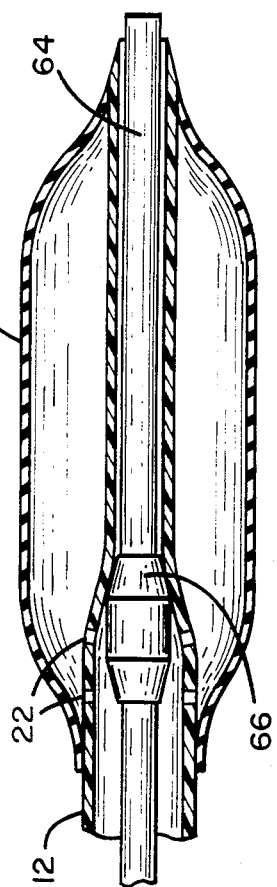
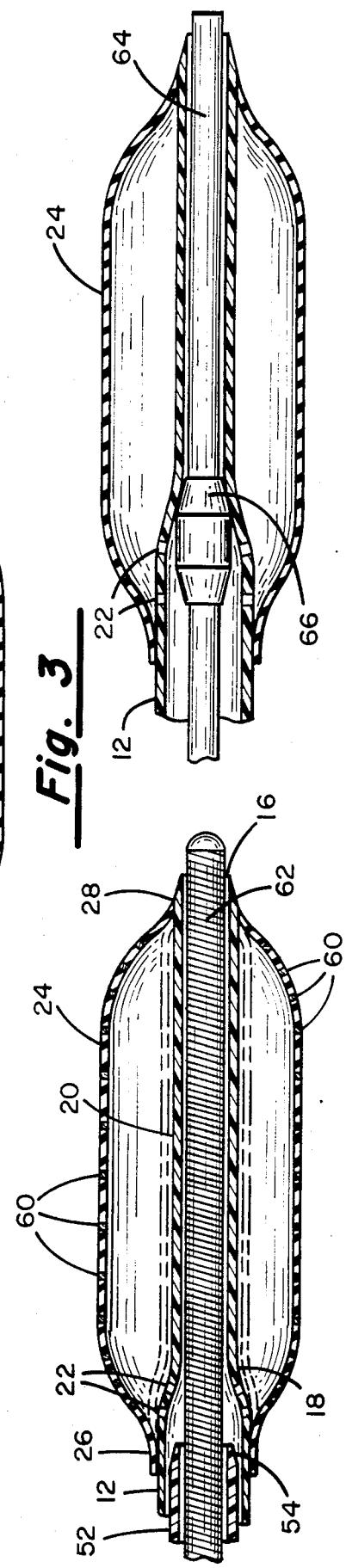

ANGIOPLASTY CATHETER ASSEMBLY

BACKGROUND OF THE INVENTION

I. Field of the Invention:

This invention relates generally to an improved catheter structure for performing cardiovascular angioplasty procedures, and more particularly to a catheter construction which permits a variety of medical procedures to be carried out using the same catheter once it has been routed appropriately through the vascular system.

II. Description of the Prior Art:

Coronary artery disease has been a major cause of death in this country for a number of years. Due to causes which are not totally understood, over a period of time, fatty deposits and plaque build up on the interior walls of the coronary arteries leading to ischema and the discomfort of angina pectoris. Also, the narrowed coronary arteries can become blocked by thrombotic material carried in the bloodstream and, once blocked, may result in a coronary infarct.

For a number of years, coronary bypass surgery has been the procedure used to treat coronary artery disease, especially where a drug regimen has proven unsuccessful. In carrying out this treatment, the chest is opened to expose the heart, and blocked segments of coronary arteries are bypassed, using a vein harvested from the patient's own leg. Because of the traumatic nature of the surgical procedure, a prolonged hospitalization is generally required as well as an extended recuperative period.

In a paper entitled, "Nonoperative Dilation of Coronary-Artery Stenosis—Percutaneous Transluminal Coronary Angioplasty", which was published in *The New England Journal of Medicine*, Vol. 301, No. 2, Pgs. 61-68 (July 12, 1979), A. Gruntzig, et al disclosed a technique for opening partially occluded coronary blood vessels by inserting a catheter into the femoral artery and routing same through the vascular system and into a coronary artery. This catheter incorporates a ballon-type expander near the distal end thereof. Once the catheter is positioned with the uninflated balloon in the area occupied by the stenotic lesion, inflation of the balloon has the effect of opening the theretofore partially occluded coronary artery and restoring its patentcy.

In the Schjeldahl et al U.S. Pat. No. 4,413,989, assigned by mesne assignment to applicants' assignee, there is described a PTCA catheter having provision for profusing fluids, including blood, from the proximal end of the catheter out its distal end so that even when the balloon is inflated during the angioplasty procedure, the cells downstream from the site of the lesion being treated will not be starved of blood. The amount of fluid perfused is governed by the pressure applied at the proximal end and the size of the distal orifice through which the fluid passes. In one arrangement shown in the aforereference U.S. Pat. No. 4,413,989, a coaxial arrangement of an outer tube and an inner tube was provided and the inner tube extended beyond the distal end of the outer tube. The distal portion of the inner tube was then enlarged and the enlargement could be brought into engagement with the distal opening in the outer tube to function as a valve by manipulating the inner tube at its proximal end. In this manner, the rate of flow of fluids out the distal end of the outer tube can be regulated.

While the device described in the aforereferenced Schjeldahl et al patent provides a practical angioplasty catheter, it lacks the versatility of the angioplasty catheter of the present invention. As will be described in considerable detail hereinbelow, the catheter of the present invention can be used in a perfusing mode in which a substantial flow of blood or blood components may be perfused distally of the treatment site. In another mode, a guide wire may be inserted through the lumen of the catheter, thus narrowing the passageway through which the perfusate may flow while facilitating the routing of the catheter into the appropriate arterial branch to be treated. By utilizing a third element, namely, an inner tube coaxially disposed within the outer tube, and by appropriately manipulating the proximal end of the inner tube, it may be made to engage the inside walls of the outer tube in a sealing arrangement whereby the inflation and deflation of the expander member is facilitated. By partially withdrawing the inner tube, the flexibility of the distal portion of the catheter can be increased which facilitates the ability of the catheter to track or follow the guide wire. Finally, the guide wire and the inner tube may be totally removed from the lumen of the outer tube and replaced with an optical fiber bundle so that stenotic lesions can be lased and the site simultaneously aspirated to remove any debris created by this process.

SUMMARY OF THE INVENTION

In accordance with one form of the invention, the percutaneous, transluminal coronary angioplasty (PTCA) catheter may comprise an elongated, flexible, plastic outer tubular member having three integrally formed segments, one of the segments being of a first outer diameter, another being of a second outer diameter less than the first and the third being a transition zone between the first and second segments. At least one aperture is formed through the wall of the outer tubular member in the transition zone and an expander is bonded to the outer surface of the outer tubular member so as to span the aperture(s). An elongated, flexible, plastic inner tubular member, whose outside diameter is such that the inner tubular member may be slidingly received within the lumen of the outer tubular member within the first segment but not within the second segment is provided, and the distal end of the inner tubular member is shaped to seat in a sealing relation with the inner side wall of the outer tubular member within the transition zone. Completing the assembly is a specially designed hub attached at the proximal end of the catheter and which is configured to allow the introduction of fluid between the outside surface of the inner tubular member and the inside surface of the outer tubular member. Also, the hub allows reciprocal movement of the inner tube within the lumen of the outer tube to engage and disengage the seal. Moreover, provision is made for introducing a guide wire through the lumen of the inner tube. Both the guide wire and the inner tube may be removed from the lumen of the outer tube so as to maximize the flow rate of fluids introduced at the proximal end of the catheter or the substitution of a fiber optic bundle if the PTCA catheter is to use a laser beam to remove the stenotic lesion being treated.

OBJECTS

It is accordingly a principal object of the present invention to provide an improved catheter for performing coronary transluminal angioplasty.

Another object of the invention is to provide a PTCA catheter of a relatively small outside diameter when its expander is noninflated.

Yet another object of the invention is to provide a PTCA catheter in which the flow of fluids out the distal end or the rate of aspiration can be controlled by the surgeon during the catheter's use.

A still further object of the invention is to provide a PTCA catheter in which the expander pressure and rate of distal perfusion can be regulated.

These and other objects and advantages of the invention will become apparent to those skilled in the art from the following detailed description of a preferred embodiment, especially when considered in conjunction with the accompanying drawings in which like numerals in the several views refer to corresponding parts.

DESCRIPTION OF THE DRAWINGS

FIG. 1 is a partially cross-section view of the catheter assembly of the present invention;

FIG. 2 illustrates the distal end portion of the catheter of FIG. 1 showing the seal in its open condition;

FIG. 3 illustrates the catheter of FIG. 1 with all inner members removed; and

FIG. 4 illustrates the PTCA catheter of the present invention in which a fiber optic bundle replaces the inner tubular member for carrying out a different form of angioplasty.

DESCRIPTION OF THE PREFERRED EMBODIMENT

FIG. 1 is a partially cross-section view of the percutaneous transluminal angioplasty catheter comprising the preferred embodiment of the present invention. The catheter is referred to generally by numeral 10 and includes a first, outer, elongated, flexible, plastic tubular member 12 having a generally uniform outside diameter over a majority of its length but tapering in a transition zone 18 to a distal end segment 20 having a lesser outside diameter. Without intending to limit the invention in any way, but to provide an example, the outer flexible tubular member 12 may be made from polyester material and may have an outside diameter of 0.055 inches (4.5 French) over a majority of itslength but tapering down to an outside diameter of 0.030 inches proximate the distal end thereof. The corresponding inside diameter for the outer tubular member 12 are 0.044 inches and 0.020 inches, respectively. Other examples of materials from which the outer tube 12 may be fabricated are polyethylene, PVC and polyurethane.

Extending through the side wall of the outer tubular member 12 in the transition zone 18 are one or more apertures 22. Bonded to the outer surface of the outer tubular member 12 is an expander member 24, which in the view of FIG. 1 is shown in its inflated condition. More particularly, the proximal end of the tubular expander 24 is circumferentially bonded at 26 to the outer surface of the tubular member 12 proximally of the aperture 22 while its distal end is circumferentially bonded at 28 near the distal 16 end of the outer tubular member 12. Thus, the expander member 24 spans the apertures 22 allowing it to be inflated or deflated by injecting or removing fluid through the apertures 22.

The expander member 24 may be made from an extensible but inexpandable material, such as a biaxially oriented plastic material polyethylene terathalate (PET) provides an excellent choice in that it can be inflated to a pressure of up to 12 atmospheres without rupturing or unduly swelling. Alternatively, the expander member 24 may be made from an elastomeric material, such as silicone or urethane, but which incorporates circumferential fiber bands spaced from one another so as to provide a desired balloon profile when the expander member is inflated. By providing closer fiber-to-fiber spacing in the zones 26 and 28, adequate sealing of the expander member 24 to the outer surface of the tubular member 12 can be achieved.

Attached to the proximal end 14 of the outer tubular member 12 is a hub, which is indicated generally by numeral 30. The hub is seen to include a main body portion 32 having a longitudinal bore 34 extending therethrough and having externally threaded proximal and distal ends indicated by numerals 36 and 38, respectively. The distal end portion 38 of the hub body 32 is tapered in a frustoconical configuration and, in securing the outer tubular member 12 to the hub, the proximal end of the tube 12 is first flared to receive the conical tip of the body 32, and then an internally threaded end cap 40 is screwed onto the threaded portion 38 of the hub body 32 and clamps the hub body 32 to the proximal end of the tubular catheter 12.

Slidingly received within the bore 34 of the hub body 32 is a rigid tubular reinforcing stem member 42. Circling the stem 42 is a ring 44 made from a compressible material, such as latex or silicone rubber, the ring being partially retained in an annular groove formed in the proximal end 46 of the hub body member 32 and abutts the inner surface 48 of an internally threaded end cap 50 which mates with the screw threads 36 on the hub body. As can be observed from FIG. 1, when the end cap is screwed tightly onto the hub body 32, the deformable ring or sleeve 44 is squeezed tightly against the reinforcing stem 42, preventing longitudinal movement thereof within the bore 34 of the hub body 32. However, when the end cap 50 is loosened, the frictional engagement between the compressible sleeve 44 and the stem 42 is relaxed, allowing longitudinal displacement of the stem 42 within the bore 34.

With continued reference to FIG. 1, it can be seen that there is attached to the distal end of the stem 42 a second, flexible, plastic, inner tubular member 52 which is coaxially disposed within the lumen of the outer tubular member 12 and which extends substantially the entire length of the catheter, terminating in a suitable taper at its distal end 54 so as to conform to the inside wall of the outer tubular member 12 in the transition zone 18. Again, for the purpose of illustration only, with the dimensions of the outer tubular member 12 set forth above, the coaxially disposed inner tubular member 52 may be extruded from PFA TEFLON® synthetic resin polymer and may have an outside diameter of 0.032 inches and an inside diameter of 0.020 inches.

With the sizes indicated, a fluid, such as blood, radiopaque dyes, medicaments, etc., may be introduced through the luer fitting 56 formed on the hub body 32 and made to flow between the outer surface of the inner tube 52 and the inner surface of the outer tube 12. When the inner tubular member 52 is in its·forwardmost position, as illustrated in FIG. 1 with the tapered end portion 54 thereof in sealing engagement with the inner surface of the outer tubular member 12 in the transition zone 18, the fluid is essentially blocked from flowing distally of the seal and thus passes through the apertures 22 to inflate the expander member 24 to a maximum pressure established by the fluid source (not shown) attached to the luer fitting 56.

Referring next to the somewhat enlarged distal end portion of the catheter assembly of FIG. 1, the inner tubular member 52 has been pulled back (to the left in FIG. 1) so that it no longer mates in a sealing relationship with the outer tubular member 12 in the transition zone 18. Now, when fluid is introduced through the luer connector 56 and made to perfuse between the outer surface of the inner tube 52 and the inner surface of the outer tube 12, only a portion of the flow is available to fill the expander member 24 and the remaining portion of the flow perfuses out the distal end 16 of the PTCA catheter 10. The inner tubular member 52 can be locked in the retracted disposition shown in FIG. 2 by appropriately tightening the end cap 50 on the hub body 32 when the reinforcing stem 42 has been drawn rearward a desired distance.

With continued reference to FIG. 2, in this enlarged view, it is possible to see the earlier-mentioned circumferentially disposed reinforcing fibers 60 contained within the expandable silicone rubber or polyurethane material comprising the balloon 24. Note in particular that the spacing between adjacent circumferential fibers is closer in the zones 26 and 28 where the expander member 24 is bonded to the outer surface of the outer tubular member 12. These fiber bands thus limit the extent to which the expander member can be inflated and tend to ensure a stable seal.

Illustrated by the dotted lines in FIG. 2 is the disposition of the expander member 24 when suction is applied to the luer connection 56 to deflate the expander member. Because the outer tubular member tapers down to a lesser diameter in the distal zone 20, when the balloon 24 is deflated, it tightly conforms to the outside surface of the tubular member 12 and does not increase the overall diameter of the catheter, thus facilitating its routing through the patient's vascular system.

With continued reference to FIGS. 1 and 2, also facilitating the routing of the catheter through the vascular system is the ability to include a helically wound guide wire 62 which can be inserted through the tubular reinforcing stem 42 and the lumen of the inner tubular member 52 and through the constricted portion 20 of the outer tubular member and beyond the distal tip 16 of the catheter. Again, the guide wire can be sized so as to allow fluid flow between it and the inside surface of the outer tubular member. Thus, perfusion of blood distally beyond the stenotic lesion being treated can be accommodated.

To enhance the trackability of the catheter, i.e., its ability to follow the guide wire 62 around sharp bends in the vascular system, the main body portion of the tube 52 may have a hardness of about 72 D durometer whereas the distal five or so inches thereof may have a lower durometer, e.g., 55 Durometer. This allows the tip to more readily bend while the main body of the catheter is more stiff and can be pushed without buckling.

With reference to FIG. 3 where greater fluid flow may be desired during the course of a angioplasty procedure, by removing the end cap 50 from the hub 48, the entire guide wire 62 and inner tubular member 52 may be removed from the central lumen of the outer tubular member 12. The large lumen now available gives the least resistance to flow. It also reduces the pressure on the walls of the expander member 24.

In the view of FIG. 4, the inner tubular member 52 and the guide wire 62 have been removed and replaced with an optical fiber whereby laser energy may be directed onto the stenosis. By limiting the size of the optical fiber 64 relative to the size of the lumen of the outer tubular member 12, a sufficiently large lumen exists for increased effectiveness of aspiration. Thus, following a lasing step, the blood containing fatty deposits and/or gases generated during the lasing operation may be aspirated out the proximal end of the catheter hub 30. By providing the tapered enlargement 66 on the optical fiber, to act as a valve by engaging the tapered inner surface of the outer tubular member 12 in the intermediate zone 18, the balloon may be inflated during the lasing step by injecting a suitable fluid into the lumen of the outer tubular member 12 and allowing it to flow through the apertures 22 into the interior space defined by the balloon 24. The inflation of the balloon 24 allows it to act as a positioning stop and, by retracting the enlargement 66 in the proximal direction, it again provides a relatively large lumen for aspiration. It is also envisioned, however, that the guide wire 62 shown within the lumen of tube 52 in FIGS. 1 and 2 can be replaced with an optical fiber and then the tubular member 52 may be manipulated at its proximal end to control the inflation of the balloon and the aspiration of fluids following the lasing step.

This invention has been described herein in considerable detail in order to comply with the Patent Statutes and to provide those skilled in the art with the information needed to apply the novel principles and to construct and use such specialized components as are required. However, it is to be understood that the invention can be carried out by specifically different equipment and devices, and that various modifications, both as to equipment details and operating procedures, can be accomplished without departing from the scope of the invention itself.

What is claimed is:

1. A PTCA catheter comprising:
    (a) an elongated, flexible plastic, outer tubular member, said outer tubular member haing three integrally formed segments, the first of said segments being of a first outer diameter, the second of said segments being of a second outer diameter less than said first outer diameter and the third segment being a transition zone between said first and said second segments, said second segment leading to the distal tip of said catheter, there being an aperture through the wall of said outer tubular member in said transition zone;
    (b) an elongated, flexible plastic, inner tubular member having an outer diameter permitting said inner tubular member to be slidingly received within the lumen of said outer tubular member within said first segment, but not within said second segment, the distal end of said inner tubular member being shaped to seat in a sealing relation with the inner side wall of said outer tubular member within said transition zone; and
    (c) an expander member surrounding said outer tubular member and extending from said transition zone to the distal end of said catheter, said expander member being circumferentially bonded to said outer tubular member at two spaced apart locations on either side of said aperture.

2. The PTCA catheter as in claim 1 and further including guide wire means positionable within the lumen of said inner tubular member and the lumen of said other segment of said outer tubular member.

3. The PTCA catheter as in claim 1 and further including an optical fiber positionable within the lumen of said inner tubular member and the lumen of said other segment of said outer tubular member.

4. The PTCA catheter as in claim 1 wherein said expander member comprises a biaxially oriented plastic material.

5. The PTCA catheter as in claim 1 wherein said expander member comprises an elastomeric material having circumferential fiber bands embedded in said material to influence the radial expansion of said expander member.

6. The PTCA catheter as in claim 1 and further including hub means attached to the proximal end of said catheter for introducing a fluid in the zone between the outside of said inner tubular member and said inner side wall of said outer tubular member such that said fluid flows through said aperture when said distal end of said inner tubular member is seated in said sealing relation, and out the distal end of said outer tubular member when said distal end of said inner tubular member is not seated in said sealing relation.

7. The PTCA catheter as in claim 6 wherein said hub means comprises:
(a) a body member having a first externally threaded end and a second externally threaded end, said first threaded end being chamfered;
(b) a longitudinal bore extending through said body member from said first threaded end through said second threaded end;
(c) a first cap member having an opening therethrough for receiving a flared proximal end of said outer tubular member, and being internally threaded to mate with said first externally threaded end of said body member;
(d) a generally rigid, tubular member bonded to the proximal end of said inner tubular member and slidingly received in said longitudinal bore in said body member; and
(e) means including a second cap member having internal screw threads engageable with said second externally threaded end on said body member for frictionally securing said generally rigid tubular member in a desired position within said longitudinal bore of said body member.

8. The PTCA catheter as in claim 7 and further including a radially extending bore in fluid communication with said longitudinal bore in said body member.

9. The PTCA catheter as in claim 8 including means for injecting fluid into and drawing fluid out from said radially extending bore.

* * * * *